(12) United States Patent
Peters et al.

(10) Patent No.: US 6,455,072 B1
(45) Date of Patent: Sep. 24, 2002

(54) STABLE AQUEOUS DISPERSION OF NUTRIENTS

(75) Inventors: Scott E. Peters, Wooster, OH (US); Darryl H. Woods, Glenmont, OH (US)

(73) Assignee: Ingredient Innovations International, Wooster, OH (US)

( * ) Notice: Subject to any disclaimer, the term of this patent is extended or adjusted under 35 U.S.C. 154(b) by 0 days.

(21) Appl. No.: 09/685,366

(22) Filed: Oct. 10, 2000

Related U.S. Application Data

(60) Provisional application No. 60/161,995, filed on Oct. 28, 1999.

(51) Int. Cl.[7] .................................................. A61K 9/14
(52) U.S. Cl. ........................ 424/489; 424/400; 424/485; 424/725; 424/94.1; 424/94.3
(58) Field of Search ................................ 424/94.1, 400, 424/485, 725, 489; 514/937, 975

(56) References Cited

U.S. PATENT DOCUMENTS

| | | | | |
|---|---|---|---|---|
| 4,938,983 A | * | 7/1990 | Peignier et al. |
| 5,510,391 A | * | 4/1996 | Elson |
| 5,661,149 A | * | 8/1997 | King et al. |
| 5,827,539 A | * | 10/1998 | Gellenbeck |
| 5,925,684 A | * | 7/1999 | Schweikert et al. |
| 6,051,250 A | * | 4/2000 | Ribier et al. |
| 6,184,255 B1 | * | 2/2001 | Mae et al. |

\* cited by examiner

*Primary Examiner*—Leon B. Lankford, Jr.
*Assistant Examiner*—Ruth Davis
(74) *Attorney, Agent, or Firm*—Frommer Lawrence & Haug LLP

(57) ABSTRACT

This invention relates to a stable aqueous dispersion of nutrients and more particularly, to an aqueous dispersions of an active nutritional ingredient selected form (a) an isoflavone, (b) lycopene (c) lutein, (d) a Coenzyme $Q_n$ where n is an integer of 1 to 12, or (e) a mixture of any of the foregoing nutrients.

3 Claims, No Drawings

STABLE AQUEOUS DISPERSION OF NUTRIENTS

This application claims priority from U.S. provisional application Ser. No. 60/161,995 filed Oct. 28, 1999, which is incorporated herein by reference.

BACKGROUND OF THE INVENTION

1. Field of the Invention

This invention relates to a stable aqueous dispersion of nutrients, and more particularly, to a dispersion comprising an ingredient selected from (a) an isoflavone, (b) lycopene, (c) lutein, (d) a Coenzyme Q or (e) a mixture of the foregoing ingredients; and a stabilizer.

2. Description of the Related Art

Nutritional ingredients, such as an isoflavone, e.g. a soybean derived isoflavone, are currently available in tablets or other dry forms because heretofore they could not be satisfactorily dispersed in water. The nutritional ingredients, such as an isoflavone, lycopene, lutein, Coezyme Q's, are not ordinarily dispersable in aqueous systems because they are only slightly water or oil soluble.

These nutritional ingredients are desirable for use in beverages and cosmetics, in the form of aqueous dispersions or liposomes. For example, isoflavone is employed to treat humans to lower cholesterol, to treat solid tumors and angiogenic diseases. Additionally, it reduces bone calcium loss and is an antioxidant which can reduce free-radical damage to cells. Accordingly, a means for rendering these ingredients water dispersible is needed and desired.

SUMMARY OF THE INVENTION

This invention relates to a stable suspension comprising a nutrient or nutritional ingredient and a stabilizer therefor dispersed in an aqueous system, e.g. a solvent comprising water. In particular, the ingredient is a nutrient selected from the group of (a) an isoflavone (b) lycopene, (c) lutein, (d) a Coenzyme $Q_n$, where n is an integer of 1 to 12, (e) a mixture of any of the foregoing ingredients.

DETAILED DESCRIPTION OF THE INVENTION

This invention involves a stable aqueous suspension which comprises a nutrient and a nutrient stabilizer dispersed in an aqueous system or solvent, e.g. water.

A suitable nutrient or nutritional ingredient is one which is suitable for therapeutic treatment of an animal, e.g. a human being, by ingestion, e.g. via a beverage, or a topical application, e.g. via a lotion or cream, but which is unfortunately typically insoluble or only slightly soluble in water at room temperature, e.g. 20° C. to 25° C. It is these ingredients which are the subject of this invention. Some suitable nutrients or nutritional ingredients include (1) a compound of the formula,

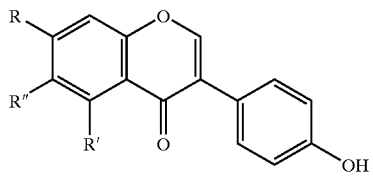

where R is OH, β-glucoside, 6"-O-acetylglucoside, or 6"-O-malonylglucoside; R' is H or OH; and R" is H or OCH$_3$; such as isoflavone, e.g. a soybean derived isoflavone, and a substituted isoflavone, such as daidzein, genistein and glycitein; (2) lycopene, (3) lutein, (4) a Coenzyme $Q_n$, where n is an integer of 1–12, e.g. Coenzyme $Q_{10}$, and (5) a mixture of any of the foregoing ingredients.

For purposes of the dispersions of this invention, which are intended for therapeutic use or as additives in association with therapeutic treatment of animals, e.g. a human, the particular nutrient or mixture of nutritional ingredients is present in the inventive aqueous dispersions in an effective nutritional amount, that is an amount which causes its desired nutritional or therapeutic effect.

The term "amount" as used herein refers to quantity or concentration as appropriate to the context. The amount of nutrient that constitutes a nutritional amount varies according to factors such as potency of the particular ingredient or mixture of ingredients, the route of administration and the mechanical system used to administer the dispersion. A nutritionally effective amount of a particular nutrient can be selected by those or ordinary skill in the art with due consideration of such factors. Generally, a nutritionally effective amount will be from 0.005 parts by weight to about 10 parts by weight based on 100 parts by weight of the dispersion.

A suitable aqueous system or medium is selected. A suitable aqueous system or medium for the dispersions of this invention include water and an aqueous solution of an organic alcohol of 1 to 6 carbon atoms, e.g. ethanol, propylene glycole, glycerine, etc., and a mixture of the foregoing; present in an amount of up to ten percent (10%) by weight. The aqueous system is one which will permit a stable dispersion to be formed therein when combined with the selected nutrient or mixture of nutrients, which in turn is destined to be combined with a suitable nutrient stabilizer. The aqueous system is present in an amount which affords the desired dispersion and is dependent upon the selected nutrient or mixture of nutritional ingredients with the selected nutrient stabilizer. Typically, the aqueous system comprises 75 to 95 weight percent of the dispersion.

A suitable stabilizer is selected. A suitable stabilizer includes (1) a lecithin, derived from soybean or egg which contain a complex mixture of phospholipids consisting mainly of phosphatidylcholine, phosphatidylethanolamine, phosphatidylinositol, and phosphatidic acid combined with varying amounts of other substances such as triglycerides; the lecithin can be of standard grade or can be modified or refined lecithin e.g. deoiled, hydrogenated, hydroxylated, enzyme modified, acetylated, etc.; (2) a hydrocolloid, e.g. xanthan gum, a pectin, gelatin, guar gum, carrageenan; (3) a surfactant, e.g. cetylpyridinlium chloride, polysorbate 80, sorbitan monostearate, polyglycerolesters, block copolymers of propylene oxide, ethylene oxide; (4) a DOWICIL, a product of Dow Chemical Co., e.g. DOWICIL 200 (cis isomer 1-(3-chloroallyl)-3,5,7-triaza-1-azonia adamantane chloride) of the formula,

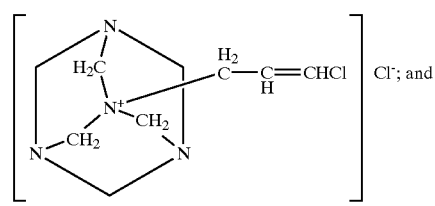

(5) a mixture of any of the foregoing stabilizers.

An aqueous dispersion of the selected nutrient comprises the nutrient stabilizer in an amount effective to stabilize the aqueous dispersion relative to an identical aqueous formulation or mixture not containing the nutrient stabilizer, such that the active ingredient does not settle, cream or flocculate after agitation so quickly as to prevent reproducibility, e.g. reproducible dosing. Reproducible application, e.g. dosing, can be achieved if the resultant aqueous suspension is substantially uniform for about 1 to 2 hours after agitation thereof.

The particular amount of stabilizer that constitutes an effective amount is dependent upon the particular stabilizer, the particular aqueous system or medium employed and the particular nutritional ingredient or mixture of ingredients employed. It is therefore not practical to enumerate a specific effective amount for use with specific dispersions or formulations of the invention, but such amount can readily be determined by those skilled in the art with due consideration of the factors set forth above. Generally, however, the stabilizer can be present in a formulation in an amount from about 0.05 percent by weight to about 10 percent by weight, more preferably about 0.2 percent to about 5 percent by weight, based on the weight of the dispersion or formulation.

Typically, the nutrient stabilizer DOWICIL 200 (cis isomer 1-(3-chloroallyl)-3,5,7-triaza-1-azonia adamantane chloride) preservative is combined with; the aqueous system, e.g. water, at a temperature of 20° to 70° C. and is mixed for 2 to 10 minutes. Thereafter the active ingredient or nutritional agent, e.g. isoflavone, is added thereto to form a mixture. The resultant mixture is then subjected to a microfluidization treatment using any commercially available microfulidizer, e.g. Microfluidics M110, at a minimum shear pressure of 6500–7000 psi, preferably at a sheer pressure of 6500 to 8000 psi, and most preferably at a shear pressure of 7000 to 7500 psi, whereby a particle size to the active ingredient typically is less than 500 nm, preferably less than 300 mn, most preferably less than 250 nm, to form the desired aqueous dispersion.

It is noted that the procedure described above can be modified, namely the stabilizer is added to the resultant aqueous dispersion, i.e. subsequent to the described microfluidization of the mixture of the nutrient combined with the aqueous system.

The resultant aqueous nutrient dispersion can then be further formulated and administered to a patient, e.g. a mammal such as a human being, by any conventional means, such as topically, orally; etc. Typically the dispersion is combined with other drugs, adjuvants, etc. in the form of a cream or lotion, e.g. a cosmetic, or in the form of a liquid, e. g. a beverage.

EXAMPLES

Example 1

SoyLife 100, a product manufactured by Schouten, Inc. 3300 Edinborough Way, Minneapolis, Minn. 55435, contains ten percent by weight of soy derived isoflavone. Ten weight percent of this material was mixed or dispersed with 0.2% by weight DOWICIL 200 and 89.8%. by weight of water using a laboratory mixer. The resultant mixture was fluidized twice through a Microfluidizer (a product manufacture by MicroFluidics, Corp.) at 7,400-psi sheer pressure and 40 psi head pressure. The resultant slurry or dispersion was homogeneous and could easily be incorporated into a skin cream formulation.

Example 2

Prevastein HC, a product of Central Soya, 1946 West Cook Road, Fort Wayne, Ind. 46801, contains 40% by weight of isoflavone. Ten weight percent of this nutrient was combined with 0.1 percent by weight of potassium sorbate and 0.1% by weight of citric acid in 89.8% by weight of water. The resultant mixture was mixed with a laboratory mixer, then fluidized twice through the microfluidizer as in Example 1, at 7500-psi sheer. Rhodigel (xanthan gum), 0.5% by weight, was added to the fluidized sample during high-speed mixing with a laboratory mixer. The resultant product was a thick viscous liquid that did not separate.

The resultant dispersion obtained in Example 2 was compared to samples prepared similarly to Example 2 but did not include a stabilizer and/or was not fluidized.

When diluting the dispersion prepared in Example 2 with water (0.25–0.5% dispersion), the nutrient remained dispersed for over a week, with very little precipitation forming. The other samples prepared were diluted at similar levels as the Example 2 sample, but these dispersions precipitated much more quickly (within 1–2 hours).

We claim:

1. A stable particulate suspension consisting essentially of,
   a nutrient selected from the group consisting of (a) an isoflavone, (b) lycopene, (c) lutein, (d) Coenzyme $Q_n$, where n is integer of 1 to 12; and (e) a mixture of any of the foregoing nutrients;
   a nutrient stabilizer which is a lecithin selected from the group consisting of a lecithin derived from soybean and a lecithin derived from egg; and
   an aqueous solvent system.

2. A stable particulate suspension consisting essentially of,
   a nutrient selected from the group consisting of (a) an isoflavone, (b) lycopene, (c) lutein, (d) Coenzyme $Q_n$, where n is integer of 1 to 12; and (e) a mixture of any of the foregoing nutrients;
   a nutrient stabilizer consisting of a surfactant selected from the group consisting of cetylpyridinium chloride, polysorbate 80, sorbitan monostearate, a polyglycerol ester, a block copolymer of propylene oxide, ethylene oxide and a mixture of any of the foregoing surfactants; and
   an aqueous solvent system.

3. A stable particulate suspension consisting essentially of,
   a nutrient selected from the group consisting of (a) an isoflavone, (b) lycopene, (c) lutein, (d) Coenzyme $Q_n$, where n is integer of 1 to 12; and (e) a mixture of any of the foregoing nutrients;
   a nutrient stabilizer which is DOWCIL.

* * * * *